(12) United States Patent
Roby

(10) Patent No.: US 7,294,357 B2
(45) Date of Patent: Nov. 13, 2007

(54) PLASMA COATED SUTURES

(75) Inventor: Mark Roby, Killingworth, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 978 days.

(21) Appl. No.: 09/965,872

(22) Filed: Sep. 28, 2001

(65) Prior Publication Data

US 2004/0167575 A1  Aug. 26, 2004

(51) Int. Cl.
  *B05D 3/06*  (2006.01)
(52) U.S. Cl. .................... 427/2.31; 427/489; 427/491
(58) Field of Classification Search ............... 427/2.31
  See application file for complete search history.

(56) References Cited

U.S. PATENT DOCUMENTS

| | | | |
|---|---|---|---|
| 3,187,752 A | 6/1965 | Glick | 128/335.5 |
| 3,280,160 A | 10/1966 | Bailey | 260/448.2 |
| 3,297,033 A | 1/1967 | Schmitt | 128/335.5 |
| 3,527,650 A | 9/1970 | Block | 117/7 |
| 3,541,127 A | 11/1970 | Beattle et al. | 260/448.8 |
| 3,629,310 A | 12/1971 | Bailey | 260/448.8 R |
| 3,755,399 A | 8/1973 | Nitzsche et al. | 260/448.8 R |
| 3,837,891 A | 9/1974 | Teitz | 117/46 FA |
| 3,839,297 A | 10/1974 | Wasserman et al. | 260/78.3 R |
| 3,942,523 A | 3/1976 | Rudtke | 128/132 D |
| 4,105,304 A | 8/1978 | Baker | 351/47 |
| 4,184,004 A | 1/1980 | Pines et al. | 442/102 |
| 4,185,637 A | 1/1980 | Mattei | 606/230 |
| 4,207,071 A | 6/1980 | Lipowitz et al. | 8/115.6 |
| 4,217,228 A | 8/1980 | Koerner et al. | 252/8.84 |
| 4,283,519 A | 8/1981 | Pines et al. | 528/26 |
| 4,359,545 A | 11/1982 | Ona et al. | 252/8.61 |
| 4,429,080 A | 1/1984 | Casey et al. | 525/415 |
| 4,578,116 A | 3/1986 | Rott et al. | 106/18.12 |
| 4,617,340 A | 10/1986 | Tanaka et al. | 524/588 |
| 4,624,676 A | 11/1986 | White et al. | 8/115.56 |
| 4,699,967 A | 10/1987 | Eichenauer et al. | 528/29 |
| 4,784,665 A | 11/1988 | Ona et al. | 8/115.6 |
| 4,937,277 A | 6/1990 | O'Lenick, Jr. | 524/318 |
| 5,019,093 A | 5/1991 | Kaplan et al. | 606/228 |
| 5,059,213 A | 10/1991 | Chesterfield et al. | 606/228 |
| 5,338,770 A | 8/1994 | Winters et al. | 523/112 |
| 5,383,903 A | 1/1995 | Totakura | 606/228 |
| 5,463,010 A | 10/1995 | Hu et al. | 528/25 |
| 5,541,167 A | 7/1996 | Hsu et al. | 514/56 |
| 5,955,588 A | 9/1999 | Tsang et al. | 536/21 |
| 6,263,249 B1 | 7/2001 | Stewart et al. | |
| 6,613,432 B2 * | 9/2003 | Zamora et al. | 428/409 |
| 2002/0169493 A1 | 11/2002 | Widenhouse et al. | |
| 2003/0074022 A1 | 4/2003 | Roby | |

OTHER PUBLICATIONS

PCT Search Report.
Kim et al. "Thermal and Structural Analysis of Heparin-PEO-PDMS-PEO-Heparin Pentablock Copolymers", Journal of Applied Polymer Science 1994, 54(12), 1863-1872.
H. Yasuda, "Plasma Polymerization", Academic Press, Inc, pp. 1-431 (1985).

* cited by examiner

*Primary Examiner*—Erma Cameron

(57) ABSTRACT

Suture filaments coated by a plasma polymerization process exhibit a good balance of knot run down and knot security characteristics, superior tissue drag characteristics, and improved fray resistance.

17 Claims, No Drawings

PLASMA COATED SUTURES

BACKGROUND

1. Technical Field

The present disclosure relates generally to coatings for filaments. More particularly, the present disclosure relates to silicone coatings for filaments or sutures formed by a plasma polymerization process.

2. Background of Related Art

Many synthetic materials are presently used as surgical sutures. These materials may be used as single filament strands, i.e., monofilament sutures, or as multifilament strands in a braided, twisted or other multifilament construction. Synthetic sutures have been made from materials such as polypropylene, nylon, polyamide, polyethylene, polyesters such as polyethylene terephthalate, and segmented polyether-ester block copolymers. In addition, absorbable synthetic sutures have been prepared from synthetic polymers such as polymers containing glycolide, lactide, dioxanone, caprolactone, and/or trimethylene carbonate. Natural materials have also been used to make sutures. For example, silk has been used to make non-absorbable sutures. As another example, catgut sutures are absorbable sutures made from a natural material.

Sutures intended for the repair of body tissues must meet certain requirements: they must be non-toxic, capable of being readily sterilized, they must have good tensile strength and have acceptable knot-tying and knot characteristics. The sutures should also be sufficiently durable from the point of view of fray resistance.

The performance of a suture in terms of knot run down, knot security and tissue drag are particularly important to surgeons. Knot run down performance, which reflects the ease of placement of a knot tied in a suture, is important in surgical procedures where it is necessary that a knot be tied in a suture when the knot is deep inside a surgical or natural opening. For instance, a dental surgeon may need to tie a knot inside a patient's mouth. An intravaginal hysterectomy requires suturing in restricted quarters. One technique frequently used is to tie a square knot that can be run down from an exterior location where the knot is first tied to lie against tissue with a desired degree of tightness. The knot is snugged down so that it is holding with a degree of firmness chosen by the surgeon for a particular situation and then additional throws, utilized to form additional knots, are tied down against the first throws of the square knot. In some instances, the first throw is a double twist followed by a single throw to form a surgeons' knot, with additional throws to form additional square knots on top as needed. The ease with which a knot runs down the suture depends on a number of factors such as composition of the suture, braid structure of the suture, and the nature of the coating, if any, applied to the suture. Preferably, the knot runs down the suture smoothly and easily.

Knot security is the ability of the knot to hold without slipping for an acceptable length of time. The characteristics of the suture material which allow a knot to hold securely are somewhat at odds with the characteristics of the suture material which provide satisfactory knot run down performance, since knot security requires that the suture grab itself while knot run down requires that the suture pass smoothly over itself. Accordingly, a balance of these two characteristics is normally required.

Some synthetic sutures, especially polypropylene monofilament sutures, have a tendency to fray as the suture passes over itself, e.g., when tying knots. While the limited amount of fraying exhibited by these sutures does not substantially hamper the performance of the suture, there remains room for improvement in the processing and the characteristics of such sutures.

It is also desirable for a suture to have low tissue drag, which is a measure of the force required to pull a suture through tissue. High drag forces result in chatter as the suture passes through tissue, make it more difficult for the surgeon to align tissue neatly, and increase the time to complete the closure being made with the suture.

A wide variety of coatings have been applied to sutures of various types to improve one or more characteristics of the suture. See, for example, U.S. Pat. Nos. 3,187,752; 3,527,650; 3,942,523; 4,105,304; and 4,185,637. These coatings include silicones. See U.S. Pat. No. 3,187,752.

Fibers or textile treatments which include organo silicon compounds have been described in, inter alia, U.S. Pat. Nos. 3,280,160; 3,418,354; 4,283,519; 4,359,545; 4,217,228; 4,784,665; 3,837,891; 4,207,071; 4,184,004; 4,578,116; 4,937,277; 4,617,340; and 4,624,676.

Siloxane-oxyalkylene copolymers have been described in U.S. Pat. Nos. 3,629,310; 3,755,399; 3,280,160; 3,541,127; and 4,699,967. U.S. Pat. No. 5,383,903 discloses coating a surgical suture with a dimethylsiloxane-alkylene oxide copolymer lubricant.

The above coatings are applied by means known to those skilled in the art, e.g., dipping, spraying, etc.

It would be advantageous to apply coatings possessing improved mechanical strength to sutures in order to further enhance the sutures' handling characteristics.

SUMMARY

It has now been found that a suture coated by a plasma polymerization process whereby a siloxane monomer is polymerized onto the suture surface exhibits a good balance of knot run down and knot security characteristics, superior tissue drag characteristics, and improved fray resistance.

In another aspect, the present disclosure embraces a method for improving the handling characteristics of a suture by utilizing a plasma polymerization process to apply to the suture a coating comprising a siloxane polymer.

Preferred coatings are formed by a plasma polymerization process whereby aliphatic hydrocyclosiloxane monomers are polymerized on the surface of the suture to form a siloxane coating on the suture. In one embodiment, amine groups are introduced onto the polymer coating by co-polymerizing an organo-based monomer with the aliphatic hydrocyclosiloxane monomer or by carrying out a second plasma polymerization process for the introduction of the organo-based monomer. The amine groups on the polymer coating may then be reacted with carbonate polyoxyalkylenes to give polyoxyalkylene modified polymer coatings which enhance the handling characteristics of the coated sutures.

DESCRIPTION OF THE PREFERRED EMBODIMENTS

Sutures treated in accordance with the present disclosure can be fabricated from a wide variety of natural and synthetic fibrous materials. Such materials include non-absorbable as well as partially and fully bioabsorbable (i.e., resorbable) natural and synthetic fiber-forming polymers. Non-absorbable materials which are suitable for fabricating sutures include silk, polyamides, polyesters such as polyethylene, polypropylene, cotton, linen, etc. Carbon fibers, steel fibers and other biologically acceptable inorganic fibrous materials can also be employed. Bio-absorbable sutures may be fabricated from natural collagenous material or synthetic resins including those derived from glycolic acid, glycolide, lactic acid, lactide, dioxanone, caprolactone, polycaprolactone, epsilon-caprolactone, trimethylene carbonate, etc., and various combinations of these and related monomers. Sutures prepared from resins of this type are known in the art. See, e.g., U.S. Pat. Nos. 3,297,033; 3,839,297; and 4,429,080.

Preferably, the suture is made from a synthetic material. Suitable synthetic materials include, but are not limited to, polypropylene, nylon, polyamide, polyethylene, polyesters such as polyethylene terephthalate, segmented polyetherester block copolymers and polyurethanes.

Sutures treated in accordance with the present disclosure can have one or more filaments. When more than one filament is used, the filaments may be braided, twisted, entangled, intertwined or arranged in some other multifilament configuration. A particularly useful braid structure for sutures is the spiroid braid structure described in U.S. Pat. Nos. 5,019,093 and 5,059,213 the disclosures of which are incorporated herein by reference.

In a preferred embodiment, the sutures to be coated in accordance with the present disclosure are made of synthetic polymers.

In general, sutures treated in accordance with the present disclosure are subjected to a plasma polymerization process to form a polymer coating on at least a portion of the surface of at least one filament of the suture. The term "plasma" refers to a thermodynamically non-equilibrium gaseous complex, composed of electrons, ions, gas atoms, free radicals, and molecules in an excited state, known as the plasma state.

Plasma may be generated in a process known as plasma discharge by a number of methods including combustion, flames, electric discharges, controlled nuclear reactions and shocks. The most obvious and commonly used is electric discharge. Radio frequency ("RF") or microwave discharge are mainly used for polymerization reactions. For commercial RF generators, the frequency used in the process is dictated by the Federal Communications Commission and is set at 13.56 MHz.

Two opposing processes occur simultaneously during plasma discharge. In general, it can be said that the generation of free radicals in the vapor phase leads to the formation of thin films. However, at high power of field strength, ions are generally responsible for ablation or "etching" of the surface of any article introduced into the plasma. At very low gas or monomer flow rates, there is little polymer deposition and the deposition rate decreases with increasing discharge power. At higher flow rates, the deposition of polymer increases (linearly), but reaches a maximum with increasing discharge power and then ablation becomes more predominant.

There are two types of commercially available plasma-state polymerization systems: (a) capacitively coupled internal parallel electrodes, such as Bell Jar reactors, and (b) RF coil-inductively coupled tubular reactors. Generally, without modification, these systems are not suitable for producing the uniform single-phase coatings at high enough deposition rates and are more suitable for controlled etching of an article's surface.

The most serious shortcoming of the above-mentioned commercial systems for polymer formation is their inability to control the monomer flow to the region between the electrodes. This inability renders it impossible to achieve uniform plasma density, plasma composition, or deposition rate between the electrodes. Furthermore, because the monomer is not confined to the electrode region in these systems, the flow rate between the electrodes is significantly decreased. In addition, because of the undirected monomer flow, oily and powdery deposits of plasma polymerized monomers form throughout the plasma chamber. One way to eliminate these deposits is by restricting the flow path in the reactor chamber to the space between the electrodes, which maintains polymer deposition solely in the plasma glow zone. Thus, when the plasma glow zone is activated, the monomer or monomer mixture is continually passed through the plasma glow zone and the unused monomer or monomer mixture condenses in the cold trap.

In order to adequately form polymers on the suture surface, one must understand the limitations of the commercially available systems noted above and the parameters which affect the formation of a plasma coating or membrane. The relationship between the plasma intensity, free radical concentration, and system pressure is complex. The plasma coating parameter formula, W/FM, where W is the RF power, F is the monomer flow rate, and M is molecular weight of the monomer (see Yasuda, H., Plasma Polymerization, Academic Press, 1985) fails to address two important factors: system pressure and the plasma reactor geometry.

At a given W and F, if the system pressure increases above a given pressure, the resulting coating is no longer homogenous and a two-phase morphology coating will start to appear. This two-phase phenomenon is caused by an increase in the system pressure which decreases the mean free path of monomer free radicals and results in the monomer free radicals recombining in the gas phase before reaching the suture surface. This in turn results in deposition of plasma polymerized siloxane powder along with polymerization of free radicals on the suture surface, resulting in the two-phase coating. The W/FM parameters also will change when the geometry of the plasma reactor changes. Therefore, W/FM can be a useful plasma coating parameter only if the system is maintained at constant pressure and only if the same plasma reactor geometry is utilized.

A plasma coating system with the same reactor geometry can be used if the W/FM formula is employed as a control indicator. If the system is controlled at a given pressure, increasing W and decreasing F will likely result in etching or ablation of the suture surface. If W is decreased and F is increased, the desired coating will most likely result.

Modifications of the monomer flow rate and flow path are critical factors in avoiding two-phase coatings and obtaining the necessary high deposition rates of plasma polymerized coatings on suture surfaces. In general, a high flow rate (about 5 μmole/sec), moderate R.F. power (about 80 W), and low system pressure (about 40 mTorr) will produce a suitable homogeneous siloxane coating.

The monomers used to form the polymer coating are polymerized directly on the suture surface using plasma-state polymerization techniques generally known to those skilled in the art. See Yasuda, Plasma Polymerization, Academic Press Inc., New York (1985), incorporated herein by reference.

In brief, the monomers are polymerized onto the suture surface by activating the monomer in a plasma state. The plasma state generates highly reactive species, which form the characteristically highly cross-linked and highly-branched, ultra-thin polymer coating, which is deposited on the suture surface as it moves through the area of the reactor having the most intense energy density, known as the plasma glow zone.

For plasma polymerization to produce a coating on a suture, which may also be called "plasma grafting", a suitable organic monomer or a mixture of monomers having polymerizable unsaturated groups is introduced into the plasma glow zone of the reactor where it is fragmented and/or activated forming further excited species in addition to the complex mixture of the activated plasma gases. The excited species and fragments of the monomer recombine upon contact with the suture surface to form a largely undefined structure which contains a complex variety of different groups and chemical bonds and forms a highly crosslinked polymer coating on the suture surface. If $O_2$, $N_2$, or oxygen or nitrogen containing molecules are present, either within the plasma reactor during the polymer coating process, or on exposure of the polymer coated suture to oxygen or air subsequent to the plasma process, the polymeric deposit will include a variety of polar groups.

The amount and relative position of polymer deposition on the sutures is influenced by at least three geometric factors: (1) location of the electrodes and distribution of charge; (2) monomer flow; and (3) suture position within the reactor relative to the glow region. In the case of suture fibers which are pulled continuously through the plasma chamber, the influence of the suture position is averaged over the length of the fibers.

In practice, an electric discharge from an RF generator is applied to the "hot" electrodes of a plasma reactor. The selected monomers are introduced into the reactor and energized into a plasma, saturating the plasma glow zone with an abundance of energetic free radicals and lesser amounts of ions and free electrons produced by the monomers. As the suture passes through or remains in the plasma glow zone, the surface of the suture is continually bombarded with free radicals, resulting in the formation of the polymer coating.

In one embodiment, the plasma chamber used for plasma polymerization has capacitively coupled plate-type electrodes. The sutures are exposed to monomers having a mass flow rate in the range from about 50 to about 100 standard cubic centimeters per minute (sccm), at an absolute pressure in the range from about 40 mTorr to about 70 mTorr. The exposure time ranges from about 45 seconds to about 9 minutes. The currently preferred exposure time is in the range from about 2 minutes to about 6 minutes. A radio frequency of 13.56 MHz in the range from about 25 watts to about 100 watts generates sufficient energy to activate the monomers.

It will be appreciated by those skilled in the art that in a differently configured plasma chamber, the monomer flow rate, power, chamber pressure, and exposure time may be outside the ranges of that set forth for the embodiment discussed above.

During the plasma polymerization process, the suture is subjected to both thermal and ultra-violet (UV) radiation. The heat generated can be removed by external fans constantly blowing onto the system. The heat generated by electrons, ions, or free radicals colliding with the suture surface is insignificant and will not effect the bulk mechanical properties of the suture. While the total energy released as heat or mechanical energy after impact is relatively small, the surface of the suture may become chemically active and unstable.

The UV radiation generated from the plasma process can be harmful to polymeric sutures, such as polypropylene fibers. The UV radiation penetrates the surface of the suture, breaking the polymer chains at the surface. This is known as chain scission. The polymer chains may subsequently recombine. If polymer chain scission is the dominant process, the suture's mechanical strength will be weakened. If polymer chain recombination is the dominant process, the polymer units will form local cross-linked network structures, and the suture will lose ductility and become brittle. Accordingly, the intensity of the plasma glow zone, the substrate residence time in the plasma glow zone, and the substrate pulling tension need to be carefully controlled in order to achieve a proper balance between scission and recombination and minimize the plasma-induced damage to the suture.

Where the proper balance between scission and recombination is achieved, the plasma polymerization process not only forms a thin layer of polymerized siloxane on the surface of the suture but, as noted above, the thermal and UV radiation generated by the plasma process also activates the surface of the suture itself, permitting crosslinking of the siloxane coating with the polymeric suture material. The crosslinking of the siloxane coating with the suture surface increases the mechanical strength of the suture material, which enhances the fray resistance of the suture without substantially changing its bulk properties.

In accordance with the present disclosure, siloxane monomers are used in the plasma polymerization process to produce polymer coatings on the suture surfaces. One preferred polymer coating which can be deposited on the suture surface through the plasma state polymerization process of the present disclosure uses aliphatic hydrocyclosiloxane monomers of the general formula:

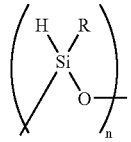

where R is an aliphatic group and n is an integer from 2 to about 10, preferably 4 to 6.

Preferred aliphatic hydrocyclosiloxane monomers include: 1,3,5,7-tetramethylhydrocycltetrasiloxane ("TMCTS"); 1,3,5,7,9-pentamethylhydrocyclopentasiloxane ("PMCTS"); 1,3,5,7,9,11-hexamethylhydrocyclohexasiloxane ("HMCHS") and a mixture of 1,3,5,7,9-pentamethylcyclosiloxane and 1,3,5,6,9,11-hexamethylcyclohexasiloxane monomers ("XMCXS"). Use of a radio frequency power greater than 5 W, a system pressure less than 300 mTorrs, and a monomer flow rate greater than 1 μmole/sec, will cause a homogeneous, hard, hydrophobic, biocompatible, polymer coating with a low friction coefficient to form on the suture surface passing through the plasma glow zone.

The aliphatic hydrocyclosiloxane monomers noted above may be used to create a homogeneous coating on the suture surface. In another embodiment, the aliphatic hydrocyclosiloxane monomers may be mixed with co-monomers to give polymer coatings having properties different from the properties of the homogenous coating. For example, by introducing reactive functionalizing monomers, or organo-based monomers, or fluorocarbon monomers together with the aliphatic hydrocyclosiloxane monomers in the plasma polymerization system, physical pore size and chemical affinity of the plasma copolymerized aliphatic hydrocyclosiloxane coating with selective monomers can be controlled. This allows the use of the copolymerized plasma polymer coating for applications which require the coating to differentiate between certain types of gases, ions, and molecules and it also may be utilized to introduce functional groups to the polymer coating which, in turn, can impart enhanced handling characteristics to the suture and also help link other compounds or compositions to the polymer coating.

In a preferred embodiment, the polymer coatings may be produced by a plasma co-polymerization process of mixtures of the same aliphatic hydrocyclosiloxane monomers noted above with organo-based monomers that introduce amine groups onto the polymer coating and form amine grafted polymer coatings. It is more preferred to introduce these organo-based monomers onto the polymer coating in a second plasma grafting process which occurs after the plasma polymerization of the aliphatic hydrocyclosiloxane monomers. Suitable organo-based monomers include allylamine, N-trimethylsilylallylamine, unsaturated amines (both N-protected and N-unprotected), and cyclic aliphatic amines (both N-protected and N-unprotected). As used herein, the term "amine grafted polymer coatings" refers to a polymer coating containing amine groups, which can be obtained either by co-polymerization of the organo-based monomer with the hydrocyclosiloxane monomer or by plasma grafting the organo-based monomer onto a previously formed siloxane polymer coating.

In yet another embodiment, these plasma treated sutures, possessing amine grafted polymer coatings, are then reacted with carbonate-based polyoxyalkylene compounds to produce polyoxyalkylene modified polymer coatings. In a preferred embodiment, the carbonate-based polyalkylene oxide is of the general formula

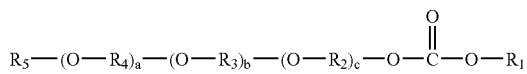

wherein $R_1$ is an N-benzotriazole group, an N-2-pyrrolidinone group, or a 2-oxypyrimidine group; $R_2$, $R_3$ and $R_4$ are independently selected alkylene groups of about 2 to about 3 carbon atoms and may be the same or different; $R_5$ is selected from hydrogen, methyl, a carbonyloxy-N-benzotriazole group, a carbonyloxy-N-2-pyrrolidinone group, and a carbonyl-2-oxypyrimidine group; a is an integer from 1 to 1000 and each of b and c is an integer from 0 to 1000, where a+b+c is an integer from 3 to 1000. Suitable lower alkylene groups include those having about 2 to about 3 carbon atoms.

In preferred compounds of the above formula, $R_2$, $R_3$ and $R_4$ is —(CH$_2$CH$_2$)— or —CH$_2$CH(CH$_3$)— or any combination thereof. More preferably $R_2$, $R_3$ and $R_4$ are ethylene. According to a preferred aspect a, b, and c are selected so as to give a molecular weight for the PEG moiety of about 500 to about 20,000, more preferably from 3000 to 4000. Preferred polyoxyalkylene carbonates include, but are not limited to, polyoxyethylene bis-(2-hydroxypyrimidyl) carbonate, polyoxyethylene bis-(N-hydroxybenzotriazolyl) carbonate and polyoxyethylene bis-(N-hydroxy-2-pyrrolidinonyl) carbonate.

These polyoxyalkylene modified polymer coatings impart a good balance of knot run down and knot security characteristics, superior tissue drag characteristics, and improved fray resistance to sutures. In addition, these polyoxyalkylene modified polymer coatings possess a polyoxyalkylene tether capable attaching additional compounds, including lubricants or bioactive compounds, to the polymer coating.

The resulting coating on the suture is between about 0.01 to about 10 percent by weight based upon the weight of the filament or filaments to which the coating is applied. Preferably, the coating is applied in an amount of from about 0.05 to about 7.5 weight percent. Most preferably, the amount of coating is between about 0.1 and about 5 weight percent. The amount of coating applied to the suture may be adequate to coat all surfaces of the suture. Preferably, the amount of coating applied will be that amount sufficient to improve the handling characteristics of the suture, regardless of whether the entire surface of the suture is coated. The term coating as used herein is intended to embrace both full and partial coatings.

The amount of coating composition may be varied depending on the construction of the sutures, e.g., the number of filaments and tightness of braid or twist. In a preferred embodiment, the depth of crosslinking of the silicone coating with the surface of the suture is less than about 100 Å. The coatings may optionally contain other materials including colorants, such as pigments or dyes, fillers or therapeutic agents, such as antibiotics, growth factors, antimicrobials, wound-healing agents, etc. Depending on the amount of coating present, these optional ingredients may constitute up to about 25 percent by weight of the coating.

An important feature of the present invention is the creation of a continuous thin coating. The thickness of this coating can be determined gravimetrically, and the continuity of the coating can be determined by its permeability. These factors, along with the chemical composition of the coating (i.e., carbon, silicone, oxygen, nitrogen percentages), determined by ESCA (electron spectroscopy for chemical analysis) are some of the values which change as plasma parameters are modified.

The following examples should be considered as illustrative and not as limitations of the present description. The examples show illustrative formulations and the superiority of the present coating composition in enhancing properties of sutures.

EXAMPLE 1

This experiment analyzed the fray resistance of synthetic sutures made of polypropylene (from United States Surgical, Norwalk, Conn.) treated in accordance with the present disclosure. Care was taken to minimize handling of the sutures, and whenever possible the sutures were handled with plastic forceps.

The siloxane derivative, 1,3,5,7-tetramethylhydrocyclosiloxane (TMCTS, HYDROSILOX®) was polymerized on the suture surface in a glow discharge plasma deposition lasting for varying amounts of time, forming a siloxane-coated suture. The TMCTS plasma was generated at 83 W, 55 mTorr, and a flow rate of 84 sccm. It was found that the application of the plasma coating for time periods ranging from 2 to 6 minutes formed polymer coatings that prevented the fraying of the polypropylene suture material.

In some cases, a second plasma polymerization process, or plasma grafting process, was utilized to introduce amine groups onto the polymer coating. N-trimethylsilylallylamine (TMSAA) was plasma grafted to the siloxane-coated suture for 4 minutes at 65 mTorr, 35 W, and a flow rate of 42 sccm. This process introduced a protected amine to the siloxane coating, that was subsequently modified in the next step.

Polyethylene oxide compound (PEOC) was used to prepare an activated-intermediate HPEOC, a bifunctional-crosslinker polyoxyethylene bis-(N-hydroxybenzotriazolyl) carbonate. HPEOC was then conjugated to the surface-bound primary amines during a 10 minute immersion in a solvent. During the conjugation, hydroxybenzotriazolyl carbonate was liberated and polyoxyethylene-(N-hydroxybenzotriazolyl) attached to the amine via a urethane bond.

Sutures treated pursuant to this plasma polymerization process were subjected to a test to determine their fray resistance. There were 3 sets of sutures: 1-6 possessed a thin siloxane coating; 7-12 possessed a thick siloxane coating; and 13-18 possessed a thick coating of HPEOC over siloxane. The fray test passes the suture repeatedly over itself until the suture frays and eventually breaks (i.e., suture failure). The results, which are reported as number of cycles to suture failure, are presented below in Table 1.

TABLE 1

| SUTURE | DESCRIPTION | #CYCLES TO FAILURE |
|---|---|---|
| 1 | Siloxane coating, thin | 66 |
| 2 | Siloxane coating, thin | 61 |
| 3 | Siloxane coating, thin | 68 |
| 4 | Siloxane coating, thin | 56 |
| 5 | Siloxane coating, thin | 48 |
| 6 | Siloxane coating, thin | 63 |
| 7 | Siloxane coating, thick | 28 |
| 8 | Siloxane coating, thick | 25 |
| 9 | Siloxane coating, thick | 47 |
| 10 | Siloxane coating, thick | 194 |
| 11 | Siloxane coating, thick | 32 |
| 12 | Siloxane coating, thick | 23 |
| 13 | Thick PEOC over siloxane | 952 |
| 14 | Thick PEOC over siloxane | 1500 (Stopped) |
| 15 | Thick PEOC over siloxane | 1388 |
| 16 | Thick PEOC over siloxane | 759 |
| 17 | Thick PEOC over siloxane | 4299 |
| 18 | Thick PEOC over siloxane | 2268 |

EXAMPLE 2

This experiment compared a commercially available suture, Prolene MDE643 (Ethicon, Inc.) with a Surgipro suture (United States Surgical) possessing an HPEOC conjugated siloxane coating that was prepared in accordance with Example 1 above. The knot security, determined by whether or not the knots broke or slipped, was determined for 6 of each of the above sutures and the results are presented below in Table 2.

TABLE 2

| SUTURE | BREAKING | SLIPPING |
|---|---|---|
| Prolene MDE643 | 6/6 knots broke | 0/6 slipped |
| Surgipro with HPEOC | 6/6 knots broke | 0/6 slipped |

The foregoing data show that sutures coated in accordance with this disclosure have knot security equivalent to commercially available sutures, and thus exhibit an advantageous balance combination of good fray resistance and knot security.

It will be understood that various modifications may be made to the embodiments disclosed herein. Therefore, the above description should not be construed as limiting, but merely as exemplifications within the scope and spirit of the claims appended hereto.

What is claimed is:

1. A method for improving the fray resistance of a suture comprising at least one filament, the method comprising:
applying a coating to at least a portion of a surface of the at least one filament of the suture by a plasma polymerization process of a hydrocyclosiloxane monomer of the general formula

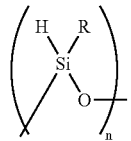

where R is an aliphatic group and n is an integer from 2 to about 10,
wherein the coating improves the fray resistance of the suture.

2. The method according to claim 1 wherein the hydrocyclosiloxane monomer is selected from the group consisting of 1,3,5,7-tetramethylhydrocyclotetrasiloxane; 1,3,5,7,9-pentamethylhydrocyclopentasiloxane; 1,3,5,7,9,11-hexamethylhydrocyclohexasiloxane and a mixture of 1,3,5,7,9-pentamethylhydrocyclopentasiloxane and 1,3,5,7,9-hexamethylhydrocyclohexasiloxane monomers.

3. The method according to claim 1 wherein the coating further comprises an amine group that has been introduced onto the coating by plasma polymerization of a gas containing a monomer selected from the group consisting essentially of unsaturated N-protected amines, unsaturated N-unprotected amines, N-protected cyclic aliphatic amines, and N-unprotected cyclic aliphatic amines, to produce an amine grafted polymer coating.

4. The method according to claim 3 wherein the unsaturated or cyclic amine is copolymerized with the hydrocyclosiloxane monomer onto the surface of the at least one filament of the suture.

5. The method according to claim 3 wherein the unsaturated or cyclic amine is plasma grafted onto the coating on the surface of the at least one filament of the suture.

6. The method according to claim 3 wherein said unsaturated or cyclic amine is N-trimethylsilylallylamine.

7. The method according to claim 3 wherein a carbonate-based polyalkylene oxide compound is contacted with the amine grafted polymer coating to produce a polyoxyalkylene modified polymer coating, the carbonate-based polyalkylene oxide compound comprising the general formula

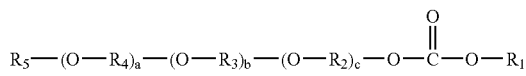

wherein $R_1$ is selected from an N-benzotriazole group, an N-2-pyrrolidinone group, or a 2-oxypyrimidine group; $R_2$, $R_3$ and $R_4$ are independently selected alkylene groups of about 2 to about 3 carbon atoms and may be the same or different; $R_5$ is selected from hydrogen, methyl, a carbonyloxy-N-benzotriazole group, a carbonyloxy-N-2-pyrrolidinone group, and a carbonyl-2-oxypyrimidine group; a is an integer from 1 to 1000 and each of b and c is an integer from 0 to 1000, where a+b+c is an integer from 3 to 1000.

8. The method according to claim 7 wherein said carbonate-based polyalkylene oxide compound is polyoxyethylene bis-(N-hydroxybenzotriazolyl) carbonate.

9. The method of claim 1 wherein the suture comprises at least one polypropylene fiber.

10. A method for making a coated suture comprising:
providing a suture comprising at least one filament having a surface; and
applying a coating to at least a portion of the surface of the at least one filament of the suture by a plasma polymerization process of a hydrocyclosiloxane monomer of the general formula

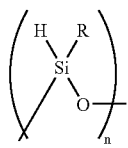

where R is an aliphatic group and n is an integer from 2 to about 10,
wherein the coating improves the fray resistance of the suture.

11. The method according to claim 10 wherein the hydrocyclosiloxane monomer is selected from the group consisting of 1,3,5,7-tetramethylhydrocyclotetrasiloxane; 1,3,5,7,9-pentamethylhydrocyclopentasiloxane; 1,3,5,7,9,11-hexamethyihydrocyclohexasiloxane and a mixture of 1,3,5,7,9-pentamethylhydrocyclopentasiloxane and 1,3,5,7,9,11-hexamethylhydrocyclohexasiloxane monomers.

12. The method according to claim 10 wherein the coating further comprises an amine group that has been introduced onto the coating by plasma polymerization of a gas containing a monomer selected from the group consisting essentially of unsaturated N-protected amines, unsaturated N-unprotected amines, N-protected cyclic aliphatic amines, and N-unprotected cyclic aliphatic amines, to produce an amine grafted polymer coating.

13. The method according to claim 12 wherein the unsaturated or cyclic amine is copolymerized with the hydrocyclosiloxane monomer onto the surface of the at least one filament of the suture.

14. The method according to claim 12 wherein the unsaturated or cyclic amine is plasma grafted onto the coating on the surface of the at least one filament of the suture.

15. The method according to claim 12 wherein said unsaturated or cyclic amine is N-trimethylsilylallylamine.

16. The method according to claim 12 wherein a carbonate-based polyalkylene oxide compound is contacted with the amine grafted polymer coating to produce a polyoxyalkylene modified polymer coating, the carbonate-based polyalkylene oxide compound comprising the general formula

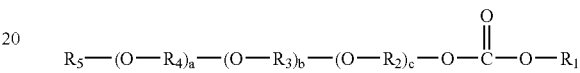

wherein $R_1$ is selected from an N-benzotriazole group, an N-2-pyrrolidinone group, or a 2-oxypyrimidine group; $R_2$, $R_3$ and $R_4$ are independently selected alkylene groups of about 2 to about 3 carbon atoms and may be the same or different; $R_5$ is selected from hydrogen, methyl, a carbonyloxy-N-benzotriazole group, a carbonyloxy-N-2-pyrrolidinone group, and a carbonyl-2-oxypyrimidine group; a is an integer from 1 to 1000 and each of b and c is an integer from 0 to 1000, where a+b+c is an integer from 3 to 1000.

17. The method according to claim 16 wherein said carbonate-based polyalkylene oxide compound is polyoxyethylene bis-(N-hydroxybenzotriazolyl) carbonate.

* * * * *